(12) United States Patent
Hollenbeck et al.

(10) Patent No.: US 9,357,926 B2
(45) Date of Patent: Jun. 7, 2016

(54) 3D SCANNER WITH STEAM AUTOCLAVABLE TIP CONTAINING A HEATED OPTICAL ELEMENT

(71) Applicant: 3Shape A/S, Copenhagen K (DK)

(72) Inventors: Karl-Josef Hollenbeck, Copenhagen (DK); Bo Petersen, Dyssegård (DK); Mike van der Poel, Rødovre (DK); Thomas Moon, Copenhagen (DK); Stefan Elmsted Jensen, Virum (DK)

(73) Assignee: 3SHAPE A/S, Copenhagen K (DK)

( * ) Notice: Subject to any disclaimer, the term of this patent is extended or adjusted under 35 U.S.C. 154(b) by 0 days.

(21) Appl. No.: 14/553,588

(22) Filed: Nov. 25, 2014

(65) Prior Publication Data

US 2015/0079535 A1 Mar. 19, 2015

Related U.S. Application Data

(63) Continuation of application No. 14/383,699, filed as application No. PCT/EP2013/054803 on Mar. 9, 2013, now Pat. No. 9,204,804.

(60) Provisional application No. 61/617,782, filed on Mar. 30, 2012, provisional application No. 61/608,831, filed on Mar. 9, 2012.

(30) Foreign Application Priority Data

Mar. 30, 2012 (DK) .................................. 2012 70162

(51) Int. Cl.
*A61B 1/227* (2006.01)
*A61B 5/103* (2006.01)
*A61B 5/00* (2006.01)
(Continued)

(52) U.S. Cl.
CPC ........... *A61B 5/0084* (2013.01); *A61B 1/00096* (2013.01); *A61B 1/00101* (2013.01);
(Continued)

(58) Field of Classification Search
CPC ............. A61B 1/0096; A61B 1/00101; A61B 1/00142; A61B 1/127; A61B 1/227; A61B 1/253; A61B 1/247; A61B 5/1079; A61B 5/0088; A61C 9/0053; A61F 7/007
USPC .......................................................... 600/169
See application file for complete search history.

(56) References Cited

U.S. PATENT DOCUMENTS 4,858,001 A * 8/1989 Milbank ............ A61B 1/00142
348/335
5,533,496 A * 7/1996 De Faria-Correa
et al. .............................. 128/898
(Continued)

FOREIGN PATENT DOCUMENTS

WO WO 2010/145669 A1 12/2010

OTHER PUBLICATIONS

International Search Report (PCT/ISA/210) mailed on Aug. 27, 2013, by the European Patent Office as the International Searching Authority for International Application No. PCT/EP2013/054803.

*Primary Examiner* — John P Leubecker
(74) *Attorney, Agent, or Firm* — Buchanan Ingersoll & Rooney P.C.

(57) ABSTRACT

A 3D scanner for recording topographic characteristics of a surface of at least part of a body orifice, where the 3D scanner includes a main body having a mounting portion; a tip which can be mounted onto and un-mounted from the mounting portion, where the tip is configured for being brought into proximity of the body orifice surface when recording the topographic characteristics such that at least one optical element of the tip is at least partly exposed to the environment in the body orifice during the recording; and a heater for heating the optical element, where the heat is provided by way of thermal conduction; where the tip can be sterilized in a steam autoclave when un-mounted from the main body of the 3D scanner such that it subsequently can be reused.

9 Claims, 7 Drawing Sheets

(51) Int. Cl.
*A61B 1/00* (2006.01)
*A61C 9/00* (2006.01)
*A61B 1/04* (2006.01)
*A61B 1/06* (2006.01)
*A61B 1/12* (2006.01)
*A61B 1/24* (2006.01)
*A61B 5/107* (2006.01)
*A61B 1/05* (2006.01)
*A61B 1/253* (2006.01)
*A61C 19/04* (2006.01)
*A61F 7/00* (2006.01)
*A61F 7/12* (2006.01)

(52) U.S. Cl.
CPC ......... *A61B1/00105* (2013.01); *A61B 1/00142* (2013.01); *A61B 1/043* (2013.01); *A61B 1/05* (2013.01); *A61B 1/0684* (2013.01); *A61B 1/127* (2013.01); *A61B 1/128* (2013.01); *A61B 1/227* (2013.01); *A61B 1/24* (2013.01); *A61B 1/253* (2013.01); *A61B 5/0064* (2013.01); *A61B 5/0088* (2013.01); *A61B 5/1076* (2013.01); *A61B 5/1077* (2013.01); *A61B 5/1079* (2013.01); *A61B 5/682* (2013.01); *A61B 5/6817* (2013.01); *A61C 9/0053* (2013.01); *A61C 19/04* (2013.01); *A61F 7/007* (2013.01); *A61F 7/12* (2013.01); *A61F 2007/0005* (2013.01); *A61F 2007/0017* (2013.01)

(56) References Cited

U.S. PATENT DOCUMENTS

| | | | | |
|---|---|---|---|---|
| 5,605,532 | A * | 2/1997 | Schermerhorn | 600/169 |
| 5,647,840 | A * | 7/1997 | D'Amelio et al. | 600/169 |
| 5,741,132 | A * | 4/1998 | Usui et al. | 433/30 |
| 5,865,725 | A * | 2/1999 | Arai et al. | 600/176 |
| 7,553,278 | B2 * | 6/2009 | Kucklick | A61B 1/00135 600/114 |
| 7,946,846 | B2 | 5/2011 | Babayoff et al. | |
| 2002/0103420 | A1 * | 8/2002 | Coleman | A61B 1/00087 600/173 |
| 2005/0283065 | A1 * | 12/2005 | Babayoff | 600/407 |
| 2007/0073108 | A1 * | 3/2007 | Takahashi | 600/169 |
| 2007/0149856 | A1 * | 6/2007 | Segawa | 600/169 |
| 2008/0160477 | A1 * | 7/2008 | Stookey et al. | 433/31 |
| 2009/0017416 | A1 * | 1/2009 | Nguyen et al. | 433/30 |
| 2009/0076321 | A1 * | 3/2009 | Suyama et al. | 600/109 |
| 2009/0294313 | A1 | 12/2009 | Pacey et al. | |
| 2010/0016671 | A1 * | 1/2010 | Wieters et al. | 600/169 |
| 2011/0221878 | A1 * | 9/2011 | Kitaoka et al. | 348/66 |
| 2011/0301414 | A1 * | 12/2011 | Hotto et al. | 600/114 |
| 2012/0034573 | A1 * | 2/2012 | Erdmann et al. | 433/29 |
| 2012/0092461 | A1 * | 4/2012 | Fisker et al. | 348/46 |
| 2012/0212817 | A1 * | 8/2012 | Moore | A61B 1/00032 359/512 |

* cited by examiner

3D SCANNER WITH STEAM AUTOCLAVABLE TIP CONTAINING A HEATED OPTICAL ELEMENT

CROSS REFERENCE TO RELATED APPLICATIONS

The present application is a continuation of U.S. application Ser. No. 14/383,699, filed on Sep. 8, 2014, which is a U.S. national stage of International Application No. PCT/EP2013/054803, filed on Mar. 9, 2013, which claims the benefit of U.S. Provisional Application No. 61/617,782, filed on Mar. 30, 2012, the benefit of U.S. Provisional Application No. 61/608,831, filed on Mar. 9, 2012, and the benefit of Danish Application No. PA 2012 70162, filed on Mar. 30, 2012. The entire contents of U.S. application Ser. No. 14/383,699, International Application No. PCT/EP2013/054803, U.S. Provisional Application No. 61/617,782, U.S. Provisional Application No. 61/608,831, and Danish Application No. PA 2012 70162 are hereby incorporated herein by reference in their entirety.

FIELD OF THE INVENTION

This invention generally relates to 3D scanners. More particularly, the invention relates to 3D scanners for scanning surfaces in humid environments and/or in environments with high requirements to hygiene, such as in body orifices, where condensation on optical surfaces is likely to occur.

BACKGROUND OF THE INVENTION

In some embodiments, the invention relates to optical 3D scanning of the geometry of body orifices, in particular in-ear scanning and intra-oral scanning. Scanners for this purpose are generally handheld. In particular the parts that enter the body orifice—generally some sort of tip, must fulfill requirements to hygiene and the quality of images taken. Optical signal quality deteriorates when condensation occurs on optical elements such as lenses or filters. The afore-mentioned body orifices have a very humid, warm microclimate, so condensation will likely occur on surfaces that, prior to insertion into the body orifice, were at ambient temperature.

The prior art has several approaches to prevent condensation on the optical elements of intraoral, i.e., dental scanners.

U.S. Pat. No. 7,946,846 (Cadent Ltd) describes a tip with auxiliary nozzles that direct a stream of gas to or from the optical surfaces and the teeth, in particular where the gas is at a temperature above body temperature. A flow of ambient air around exposed tissue can however increase the risk of infections both for the patient and the dentist. An air flow can also cause pain during dental treatment, and discomfort and noise when scanning in the ear canal.

Other manufacturers of intraoral scanners use electrical elements to heat the optical elements exposed to the body orifice. These electrical elements can either be installed inside the scanner (e.g., 3M Lava C.O.S.), or externally, such that heating only occurs when the scanner is at rest outside the body orifice (e.g., Sirona Cerec has a heating element on a cart).

Manufacturers of intraoral scanners have used several approaches to providing hygiene, particularly for those parts entering the body cavity. Some manufacturers provide single-use tips (Cadent iTero). For the 3M Lava C.O.S. scanner, the manufacturer recommends single-use plastic sleeves, which however—because of a need for high image quality—have a hole where the optical elements are located, and hence additional surface sterilization by liquid agents is recommended. For at least one device (Sirona Cerec), hot air sterilization is recommended by the manufacturer. At least one scanner (3Shape TRIOS) has a removable tip that can be steam autoclaved.

Steam autoclaving is considered the safest general-purpose sterilization method, and is accordingly recommended by authorities and standardized (e.g., EN 13060). Consequently, essentially all dental practices have a least one steam autoclave, while hot-air autoclaves are uncommon. The German Federal Institute for the Prevention of Infectious Diseases (Robert Koch Institut, RKI) has published a guideline for hygiene procedures for dental devices based on the German implementation of the Medical Device Directive 93/42/EEC [1]. For instruments used in restorative treatment (like a tip on an intraoral scanner), the guideline prescribes a sequence of cleaning in an instrument washer and steam autoclaving. A similar guideline for the US has been published by the Centers for Disease Control (CDC) [2].

While thus preferable from a hygiene perspective, the combination of an instrument washer and a steam autoclave is harsh on materials and assembly agents such as glues. This is presumably is why apparently only one scanner on the market, 3Shape TRIOS, allows this optimal form of sterilization.

SUMMARY

The invention disclosed herein solves both the condensation and the sterilization problems in the optimal way. This is performed by providing a tip that both can be autoclaved and heated internally, i.e., by the handheld scanner.

Disclosed is a 3D scanner for recording topographic characteristics of a surface of at least part of a body orifice, where the 3D scanner comprises:
 a main body comprising a mounting portion;
 a tip which can be mounted onto and un-mounted from said mounting portion, where said tip is configured for being brought into proximity of said body orifice surface when recording said topographic characteristics such that at least one optical element of the tip is at least partly exposed to the environment in the body orifice during said recording; and
 a heater system for heating said optical element, said heater system comprising a source of electromagnetic energy and a receptive element configured for receiving the electromagnetic energy and converting it into heat, where the generated heat is provided by way of thermal conduction directly to said optical element or indirectly through a heat conducting element;
 where the tip can be sterilized in a steam autoclave when un-mounted from the main body of the 3D scanner such that it subsequently can be reused.

It is an advantage over the prior art that heat can be transferred to optical elements of the tip to prevent condensation, while the tip still can be autoclaved.

According to an aspect of the invention is disclosed a 3D scanner for recording topographic characteristics of a surface of at least part of a body orifice, where the 3D scanner comprises:
 a main body comprising a mounting portion;
 a tip which can be mounted onto and un-mounted from said mounting portion, where said tip is configured for being brought into proximity of said body orifice surface when recording said topographic characteristics such that at least one optical element of the tip is at least partly exposed to the environment in the body orifice during said recording; and a heater system for heating said optical element, said heater system comprising a source of electromagnetic energy and a receptive element configured for receiving the electromagnetic energy and converting it into heat, where the generated heat is provided by way of thermal conduction directly to said optical element or indirectly through a heat conducting element;

where said heating system and said tip are configured to provide that the temperature of said optical element can be raised from 20 to 32 degrees C. within at most 60 minutes in 20 degrees C. ambient temperature while the scanner is supplied with a rated power input; and where the tip can be sterilized in a steam autoclave when un-mounted from the main body of the 3D scanner such that it subsequently can be reused.

Disclosed is a 3D scanner for recording topographic characteristics of a surface of at least part of a body orifice, where the 3D scanner comprises:

a main body comprising a mounting portion;

a tip which can be mounted onto and un-mounted from said mounting portion, where said tip is configured for being brought into proximity of said body orifice surface when recording said topographic characteristics such that at least one optical element of the tip is at least partly exposed to the environment in the body orifice during said recording;

where said tip comprises at least one optical element that is at least partly exposed to the environment in the body orifice during scanning and where the optical element is glued to a sheet that is welded onto the body of the tip; and where the tip can be sterilized in a steam autoclave when un-mounted from the main body of the 3D scanner such that it subsequently can be reused.

Disclosed is a tip for a 3D scanner for recording topographic characteristics of a surface of at least part of a body orifice, where the tip comprises:

a framework comprising a first opening configured for engaging a mounting portion of a main body of a 3D scanner, and a second opening configured for allowing light received from a surface to enter the tip;

an optical element which at least partly is exposed to the environment in the body orifice during said recording; and means for providing heat to the optical element;

where the tip can be sterilized in a steam autoclave when un-mounted from the mounting portion of the 3D scanner such that it subsequently can be reused.

When scanning a body orifice of a patient using a 3D scanner, the parts engaging the body orifice must be sterile in order to avoid infections and the transfer of deceases from one patient to the next. For a 3D scanner such as the one according to the present invention, the part engaging the body orifice is a tip which accordingly either must be replaced by a new sterile tip or must be sterilized prior to scanning a new patient. It is an advantage of the present invention that the tip of the 3D scanner can be un-mounted from the mounting portion of the main body and that the tip can withstand being sterilized in an autoclave, since this allows the tip to be removed after scanning and to be sterilized alone without the need for exposing the entire 3D scanner to a sterilization procedure. After sterilization the tip can mounted on the scanner again and be reused for scanning the next patient.

In some embodiments, the tip is made capable of withstanding sterilization in an autoclave at least partly by the choice of materials. The framework of the tip may be manufactured in a material, such as PSU, which is capable of withstanding autoclave. If a heat conducting element of the tip comprises a heat conductive layer which cannot withstand the harsh treatment of an autoclave sterilization process it may be protected by a protective layer of the heat conducting element, such as a protective layer made in stainless steel.

In some embodiments, the tip is made capable of withstanding sterilization in an autoclave at least partly by heat stacking some of the components of the tip together, such as heat stacking the heat conductive element to the framework of the tip.

In some embodiments, the tip is made capable of withstanding sterilization in an autoclave at least partly by designing the tip such that all surfaces are easily accessible, e.g. by avoiding cavities in which biological material from the patient's body orifice can gather. This has the advantage that the problems for the autoclave procedure to access materials in such cavities are avoided.

In some embodiments, the source of electromagnetic energy is located in main body.

Having the electromagnetic source located in the main body instead of e.g. in the tip provides several advantages, such as in relation to the autoclaving of the tip since such sources rarely are designed to be autoclavable. Further, since the tip often is replaced after having been used a number of times, e.g. 20 times, the cost of the tip should be kept low, and the units of the 3D scanner which can be used a large number of times should not be integrated in the tip.

Electromagnetic energy in the sense of this invention can be the energy contained in a DC, pulsating DC, or AC electric current or in electromagnetic radiation or in a static or time-varying electromagnetic field.

In some embodiments, the mounting portion comprises a tube onto which the tip can be mounted onto and un-mounted from.

It is an advantage of this invention over U.S. Pat. No. 7,946,846 that heating of the optical element occurs by way of thermal conduction, not convection as in U.S. Pat. No. 7,946,846, as convection implies a risk of microbial contamination and pain for the patient.

In some embodiments, the optical element comprises a mirror, a lens, a grating, a filter, a prism, a window, and/or other optical parts. The optical element may at least partly be exposed to the environment in the body orifice during said recording.

In the context of this invention, an optical element is any element that transmits or reflects light that is employed in the 3D measurement function. The particular optical effect—if any—of the optical element is not decisive in the sense of this invention, only the possibility of condensation occurring on at least part of its surface, thus affecting the 3D measurement performance of the scanner.

Besides the at least one optical element in the tip, the 3D scanner may have at least one other optical element in the main body of the 3D scanner on which condensation can potentially occur when the scanner is used for scanning in the body orifice. This can for example be a lens, prism or a window on a tube onto which the tip can be mounted. Also the tip may have additional optical elements not exposed to the environment in the body orifice and not affected to condensation.

In the context of the present invention, the phrase "the remainder of the 3D scanner" is used in relation to the parts of the 3D scanner besides the tip, i.e. the remainder of the 3D scanner may comprise the main body with the mounting portion of the 3D scanner.

In some embodiments, the scanner is configured to provide that the heater system provides heat to the optical element during at least a part of the recording. Heating the optical element during the recording has the advantage that the scanner can be used for a period of time without the risk of the temperature of the optical element decreasing to a level where condensation of moisture on the optical element is possible.

The activation of the heating system may be controlled by a control system of the scanner, such as a control system integrated in the main body. The control system may be configured for controlling both the recording of topographic characteristics and the heating of the optical element.

The body orifice can be a human mouth in which case the 3D scanner is configured for recording the surface of the teeth and/or the gingiva in the patient's mouth. In this case the tip is preferable configured for being brought into the patient's mouth. The scanning can be based on focus scanning such as the 3Shape Trios intra-oral scanner.

In some embodiments, at least part of the receptive element is arranged at the mounting portion.

Having the receptive element being a part of the mounting portion has the advantage that the heat is produced at the mounting portion of the 3D scanner i.e. relatively close to the tip where it can be conducted to the optical element via e.g. a heat conducting element.

In some embodiments, the heating system comprises one or more elements configured for transferring the electromagnetic energy from the source to the receptive element.

This may provide the advantage that the source of the electromagnetic energy and the receptive element can be arranged at some distance between each other such that the 3D scanner can be designed more freely. While the source of electromagnetic energy often is located in the main body, the receptive element configured for receiving the electromagnetic energy and converting it into heat can e.g. be located in the tip. In such cases, the elements configured for transferring the electromagnetic energy may be configured for transferring the electromagnetic energy to the tip, e.g. by transferring the electromagnetic energy from a unit at the mounting portion to a unit at the tip. The receptive element may also be arranged as a part of the mounting portion such that the electromagnetic energy must be transferred to the mounting portion from the source.

In the context of the present invention when a feature of the tip is described in relation to the mounting portion of the main body, it is contemplated that the tip is mounted on the mounting portion.

In some embodiments, at least part of the receptive element is arranged at the tip, and the elements configured for transferring the electromagnetic energy are configured for transferring the electromagnetic energy from the main body to the tip, such as from the mounting portion to the tip.

Having the receptive element being a part of the tip has the advantage that the heat may be generated immediately at or very close to the optical element it is intended to heat such that the heating of the optical element may occur with no or limited use of heat conducting elements and/or with limited dissipation of heat to other parts of the tip than the optical element.

In some embodiments, the elements configured for transferring the electromagnetic energy comprises electrical conductive elements, such as conducting wires.

In some embodiments, the 3D scanner comprises a coil arranged at the mounting portion and the tip comprises an element susceptible to induction where the arrangement of the coil and the element susceptible to induction is such that energy transfer to the tip can at least partly be provided by induction. The element susceptible to induction can coincide with the receptive element, such that the element susceptible to induction is the element which converts the received electromagnetic energy into heat.

In some embodiments, the elements configured for transferring the electromagnetic energy comprises a coil arranged at the mounting portion and an element susceptible to induction arranged at the tip, where the arrangement of the coil and the element susceptible to induction is such that an energy transfer from the coil to the element susceptible to induction at least partly can be provided by induction when the tip is mounted on the mounting portion.

Transferring the electromagnetic energy by means of such an inductive coupling provides the advantage that the 3D scanner is less sensitive to manufacturing tolerances which may result in a situation with a poor physical contact or even no contact between parts of the energy transferring elements arranged on the tip and parts arranged on the mounting portion.

In some embodiments, the element susceptible to induction is configured to be heated by the induction provided energy transfer and to provide said heat directly to said optical element or indirectly by way of thermal conduction through a heat conducting element.

In some embodiments, the source of electromagnetic energy comprises a power source and the receptive element of the heater system comprises an electrical heater element, such as an electrical heater element arranged at the mounting portion.

This has the advantage that the heat is produced at the mounting portion of the 3D scanner i.e. relatively close to the tip where it can be conducted to the optical element via e.g. a heat conducting element.

In some embodiments, the electrical heater element comprises a resistive element.

In some embodiments, a thermal connection is established between the electrical heater element and the heat conducting element when the tip is arranged at the mounting portion, such that an energy transfer from the electrical heater element to the heat conducting element at least partly can be provided by thermal conduction.

In some embodiments, the receptive element coincides with the heat conducting element, such that a single element both receives the electromagnetic energy, converts it into heat, and provides the generated heat to said optical element by way of thermal conduction.

In the context of this invention, two elements are said to coincide when a single physical element has the combined functions of the two elements.

In inductive heating, heat is generated due to resistive losses related to eddy currents or due to magnetic hysteresis losses.

In some embodiments, the heat conducting element is arranged at the tip such that it can transfer heat generated by the receptive element to said optical element.

Using heat conducting element allows for a having a distance between the receptive element and the optical element thus providing a large degree of freedom in the design of the 3D scanner and its tip. Further in some cases, two or more optical elements must be heated. Having a heat conducting element distributing the generated heat may provide that only one receptive element is required.

In some embodiments, energy transfer is at least partly provided by transmission of electrical power from a power source to a receptive element on the tip. This can be obtained by arranging an electrical heater element at the tube, such as at the side of the tube or inside the tube.

In some embodiments, electrical power is transferred by means of the mounting portion, such as a cable running alongside a tube onto which the tip is mounted.

In some embodiments, the source of electromagnetic energy comprises a source of electromagnetic radiation, such as a light source, and the receptive element is configured for absorbing electromagnetic radiation and converting it into heat, i.e. energy transfer to the optical element in the tip is at least partly provided by the electromagnetic radiation, such as visible radiation and/or infrared radiation.

The source of electromagnetic radiation is preferably contained in the scanner.

The receptive element configured for absorbing the electromagnetic radiation, may be located in thermal contact with the optical element, such that heat transfer between the two elements may occur by thermal conduction. The receptive element can also coincide with the optical element. Energy transfer can be effective when the optical element itself is absorptive in the range of wavelengths emitted by the source, thus transforming radiation to thermal energy.

The light source may be used for transferring electromagnetic energy only or it may at least partly also used for the 3D measurement function. In some embodiments, one wavelength of the light source is used for heating while one or more other wavelengths are used for the 3D measurement function.

In some embodiments, the scanner's light source is configured to emit electromagnetic radiation at multiple wavelengths, such as at two or more wavelengths, the absorbing receptive element is located behind the optical element, and the optical element is transparent at one or more of the wavelengths. The absorptive receptive element is preferably capable of absorbing electromagnetic radiation with at least one of the wavelengths and converting the electromagnetic radiation into heat. A further elaboration of this example is an optical element that is reflective to wavelengths that are used in the 3D measurement function, but transmissive to those absorbed by the absorptive element.

In some embodiments, an absorptive receptive element can coincide with the optical element. In such embodiments, the scanner's light source is configured to emit electromagnetic radiation at multiple wavelengths, such as at two or more wavelengths. The absorptive receptive element is capable of absorbing electromagnetic radiation with at least one of the wavelengths and converting the electromagnetic radiation into heat. A further elaboration of this example is an optical element that is reflective to wavelengths that are used in the 3D measurement function, but absorbs other wavelengths emitted by the scanner's light source.

In some embodiments, the absorptive element can be covered by some protective material making autoclaving possible. Energy transfer by radiation may require fewer parts and hence allow a tip with a smaller cross sectional area.

In some embodiments, the mounting portion and the tip are configured such that the tip can be mounted in multiple positions, such as at least two positions.

In some embodiments, the tip can also be washed in a medical instrument washer to clean the tip after use, i.e. the tip is configured to withstand being washed in a medical instrument washer, such that it subsequently can be reused.

In some embodiments, the tip comprises a RFID unit, such that the heating function of the 3D scanner by which the tip is heated is combined with an RFID function. The RFID unit may be configured to provide that the tip can be identified, i.e. the RFID function may be used to identify tips. Different tips may be equipped with RFID tags providing signals that allow an individual identification of different tips.

In some embodiments, the 3D scanner is configured to provide that information provided by the RFID unit can be used to count the number of times each of a multitude of tips has been mounted on the scanner.

Inductive heating can be combined in function with RFID. For example, a tag can be integrated into the tip and read via the receptive element. In this way, the number of times a particular tip has been mounted can be counted, and stored either on some connected PC or written to the tag itself. This is advantageous if tips have a known and/or permitted maximum number of uses.

In some embodiments, the tip of the handheld 3D scanner is removable such that it can be mounted on and unmounted from the remainder of the 3D scanner, such as from the mounting portion and the main body of the 3D scanner. At least part of the tip can come into physical contact with the scanned body orifice. The contact may not be intentional, as optical scanning generally is a non-contact technology, but inadvertent physical contact can generally not be excluded. The remainder of the scanner, in contrast, does typically not come into contact with the body orifice when the scanner is used as intended. It is advantageous to separate the tip from the remainder of the scanner in this way, because the high hygienic requirements can be confined to the tip.

The tip can be steam-autoclaved at least at 122 degrees Celsius, and preferably at 134 degrees Celsius. Preferably the tip can be autoclaved by a class B autoclave as defined in EN 13060. The remainder of the scanner can typically not be autoclaved, but possibly, it can be disinfected and/or sterilized by other means. Preferably, the tip can be autoclaved multiple times.

The tip can be cleaned prior to steam autoclaving. One method of providing cleaning can be use of a medical/dental instrument washer. Such appliances typically reach temperatures over 90 degrees Celsius, considerably higher than household dish washers that they otherwise resemble.

During scanning, condensation on the at least one optical element in the tip can be prevented or at least significantly reduced by heating said optical element. If another optical element is arranged on the remainder of the scanner on which condensation may occur, this optical element can also be heated.

Conductive heating by transfer of waste heat as generated by other electrically powered components in the scanner, e.g., motors, data processing electronics, light source, and/or other, cannot generally alone heat the optical element in the tip to 35 degrees C., for various reasons. For one, the scanner is a medical device and therefore subject to the standard IEC 60601-1-1 in most legislations. Here, IEC 60601-1-1 is referred to in its $3^{rd}$ edition. According to IEC 60601-1-1 clause 13.1.2, a rated power input exceeding 15 W results in tight restrictions on the choice of materials, tighter requirements for protection against single fault conditions, and other. Even when more than 15 W input power were available, waste heat would also heat other surfaces of the scanner, with a risk of temperatures there surpassing the limits set by IEC 60601-1-1 chapter 11. Furthermore, to achieve electrical insulation towards the patient according to IEC 60601-1-1 chapter 8, the tip is preferably made of some insulating material with correspondingly small thermal conductivity. A tip made of metal, on the other hand, would dissipate heat, again increasing the amount of waste heat that would be necessary. In general, the tight restrictions enforced by IEC 60601-1-1 cannot be met trivially, indicating the significance of the invention described here. The rated power input is effectively restricted by at least compliance with IEC 60601-1-1.

In some embodiments, the heating functionality is integrated in the handheld scanner. In this manner, there is no need for any additional device containing an external heating element, nor is there any need for any air flow along the optical element. It is preferable that at least some degree of heating can be provided during scanning. For condensation to be avoided in practice, the optical element has to be at a temperature of at least 32 degrees C., and preferably above normal human body temperature.

For the function of heating the at least one optical element, the scanner according to this invention comprises at least one receptive element designed to convert electromagnetic energy to be to heat which is transferred at least indirectly to the optical element in the tip by way of thermal conduction.

In some embodiments, the receptive element is located outside the tip in the main body of the 3D scanner, such as on the mounting portion, and is a resistive element that generates heat to be conducted to the optical element, directly or indirectly via a thermal conducting element.

Internal heating is advantageous as it prevents condensation without time limitation, whereas the effectiveness of external heating is limited in time by the thermal inertia of the optical elements in the scanner tip.

In some embodiments, the 3D scanner comprises an electrically powered element located outside the tip in the main body of the 3D scanner, and energy is transferred to the tip by means of induction, and converted to heat by some receptive element in the tip.

In some embodiments, a combination of conductive and inductive heating is implemented in a single element.

In some embodiments, an electrically powered resistive heating element is located on the tip, with power supplied from the remainder of the handheld 3D scanner, such as from the main body of the scanner. The transfer of electrical power can be by physical contact. Other ways to transfer electrical power is by means of induction, or by wireless power transfer, or others.

Thermal conduction can be implemented by metallic and/or non-metallic elements. An example of the latter is graphite.

For those embodiments that employ inductive heating, the tip must contain a material, usually a kind of metal, that is receptive to induction heating. Because the tip preferably also should be such that is can be autoclaved, said material must also be robust to corrosion. Magnetic stainless steel fulfills both above criteria. Other metals with higher thermal conductivity than stainless steel, e.g., copper and aluminum, can be suitable for this invention after anti-corrosive surface treatment such as nickel or nickel-tin plating. Another solution is to compose a heater element within the tip of two constituents, the first being receptive to induction, and the second having a higher thermal conductivity than the first. Such a second constituent can also contain at least one non-metallic material such as graphite.

In a 3D scanner according to the present invention, heating of the optical element in the tip can be sufficiently quick for a typical intended use of the scanner. A typical intended use can be in relation to a treatment, for example a dentist's appointment or an ear examination. The heating speed requirement can be tested as follows: The entire scanner with tip is initially at 20 degrees Celsius, and this is also ambient temperature. The heating is sufficiently quick if the at least one optical element in the tip reaches 32 degrees C. within 60 minutes, while the ambient temperature remains 20 degrees C., and the total power input to the scanner is in accordance with IEC 60601-1-1, and the scanner is held in some fixture that does not provide any other source of heat and that does not touch the tip. Preferably, the 32 degrees C. are attained in 10, more preferably in 2 minutes, and even more preferably in less than 1 minute. The requirement for quick heating is another argument against the use of waste heat alone. Even if it did achieve 32 degrees at thermal equilibrium, it would take too much time to be acceptable by the typical user.

In some embodiments, said heating system and said tip are configured to provide that the temperature of said optical element can be raised from 20 to 32 degrees C. within at most 60 minutes in 20 degrees C. ambient temperature while the scanner is supplied with a rated power input, such as where the temperature of said optical element can be raised from 20 to 32 degrees C. within at most 30 minutes, such as within at most 15 minutes, such as within at most 10 minutes, such as within at most 5 minutes, such as within at most 2 minutes, such as within at most 1 minute.

To prevent condensation, the optical element must be heated to above the dew point prevalent in the body orifice. Experience shows the dew point is typically below 32 degrees C. In some embodiments of the invention, the temperature of said optical element can also be raised to above human body temperature, which is the highest possible value of the dew point in a human body orifice.

It is advantageous to maintain at least some degree of heating function during scanning in the body orifice. For a scanner with limited total power, typically less power will be available for the heating function during scanning, because the electronics active during scanning, such as the image sensor, consume power as well. When the scanner is not actively scanning, in particular before scanning, more power can be dedicated to the heating function, and it is advantageous to do so.

Achieving and maintaining some desired temperature on the optical element of the tip may require regulation, possibly implemented in an IC, e.g. PLD, CPLD, FPGA, MCU, GPU or obtained by discrete components.

An electrically powered element designed to provide electromagnetic energy to be transferred to the at least one optical element in the tip can by supplied by a dedicated, potentially isolated power supply, a battery, and/or the scanner's power supply, or other power supply.

The kinds of body origins commonly scanned with 3D scanners include the mouth and the ear canal. A 3D topography of at least some teeth is required for the manufacture of restorations and/or for orthodontic treatment. A 3D topography of at least part of the ear canal, typically at least beyond the first bend, is required for the manufacture of custom-made hearing aids.

The handheld scanner can transfer data to an external PC, which again may be connected to a display, on which some, possibly processed data from the scanning are shown. The PC, display, and power supply may be mounted in a cart, a possibly mobile container with possibly an additional function of assuring or contributing to the electrical safety of the entire system.

In some embodiments, the 3D scanner is configured for providing the heat to the optical element during the recording.

In some embodiments, the 3D scanner comprises an electrical heater element arranged at the mounting portion such that there is a thermal connection between the electrical heater element and the tip, such that the energy transfer at least partly can be provided by thermal conduction.

In some embodiments, the tip is configured such that it can be sterilized in a steam autoclave when un-mounted from the main body of the 3D scanner.

In some embodiments, the heater system comprises a source of electromagnetic energy and a receptive element configured for receiving the electromagnetic energy and converting it to heat, and providing said heat to the optical element, directly or indirectly via intermediate elements.

In some embodiments the heat conducting element comprises a multi-layer sheet comprising one or more heat conducting layers and a protective layer arranged such that it faces the mounting portion and provides mechanical protection to the heat conductive layers, the heat conductive layers having a relatively higher thermal conductivity than said protective layer.

The protective layer may provide structural stability to the heat conducting layers and hence to the heat conducting element. The layers are preferably arranged such that when the tip is arranged at the mounting portion, the protective layer is located between the heat conductive layers and the mounting portion thereby shielding the heat conducting layers from abrasion when the tip is being mounted such as being slid onto the scanner, and/or from corrosion that otherwise would occur during autoclaving or cleaning in a medical instrument washer. The protective layer can for example be made from a non-magnetic or only slightly magnetic material such as stainless steel. The layer providing thermal conductivity can for example be made of eGraf (GrafTech International Holdings Inc.), which additionally has the advantage of providing strongly anisotropic conductivity.

In some embodiments, the heat conducting layer is arranged in a recess defined in the protective layer defined e.g. by controlled etching of the protective layer.

In some embodiments, the heat conducting element and/or the heat conductive layer has an anisotropic thermal conductivity, with a higher conductivity in the direction towards the optical element than along the normal of the heat conducting layers.

This has the advantage that the heat primarily is transported towards the optical element and not towards the framework of the tip, such that when there is an efficient transfer of heat from the heat conductive element to the optical element, the heat predominantly heats the optical element and not the tip framework with its outer surfaces which may come in contact with the patient during a scanning. A heating the framework and the outer surface could potentially cause the patient significant discomfort and pose a regulatory problem. Further, the energy consumption and the heating time required for heating the optical element are reduced.

In some embodiments, the ratio between the thermal conductivity in the direction towards the optical element and the thermal conductivity along the normal of the heat conducting layers is in the range of about 2 to about 200, such as in the range of about 5 to about 150, such as in the range of about 10 to about 125, such as in the range of about 20 to about 100, such as in the range of about 25 to about 50.

In some embodiments, the multi-layer heat conducting element has a thickness which is at most 2 mm or better at most 1 mm, such as at most 0.5 mm, such as at most 0.4 mm.

In some embodiments, the means for providing heat to the optical element comprises a receptive element configured for receiving electromagnetic energy from a source of electromagnetic energy and converting it into heat.

An advantage of using a receptive element to generate the heat is that it can be located e.g. at the optical element or at an appropriate part of the mounting portion, and that only an insignificant amount of heat is generated up to the position of the receptive element.

In some embodiments, the receptive element and the optical element are arranged such that the generated heat is provided directly to the optical element by way of thermal conduction.

This has the advantage that the generated heat can be applied quickly to the optical element with only a limited loss of heat.

In some embodiments, the tip comprises a heat conducting element arranged for conducting the heat to said optical element.

Including such a heat conducting element has the advantage that the heat can be generated at one location, e.g. at a portion of the tip facing a surface of the mounting portion of the 3D scanner, and transported to the optical element, thus allowing for a more freely designing of the tip.

In some embodiments, the heat conducting element is arranged such that a thermal connection can be made between the heat conducting element and an electrical heater element of the mounting portion of the main body to the heat conducting element.

In some embodiments, the heat conducting element is mechanically constrained inside the tip such that is cannot fall out of said second opening. When the tip is mounted on the scanner, the heat conducting element then cannot fall out of the tip.

In some embodiment, the heat conducting element is mechanically constrained inside the tip such that is cannot fall out when mounted on the scanner.

In some embodiments, the heat conducting element has a geometry ascertaining that it cannot fall out of tip during use, when the tip is mounted on the scanner.

Having the heat conducting element mechanically constrained inside the tip has the advantage that in case the heat conducting element accidentally is released from the inner surface of the framework of the tip, the heat conducting element still cannot fall out of the tip and into the mouth of a patient.

In some embodiments, the optical element is attached more firmly to the heat conducting element than the heat conducting element is attached to the remaining parts of the tip.

The optical element may be mounted in such a way that the bonding to the conductive element is stronger than the bonding of the heat conducting conductive element to the tip framework, such that the optical element and the heat conductive element only can come loose as a compound, and hence the optical element cannot fall out of the tip.

This has the advantage that if the tip, e.g., is dropped on the floor, it is more likely that the heat conducting element separates from the framework of the tip than the optical element separates from the heat conducting element. The optical element alone is hence not likely to fall out of the tip. If the heat conducting element further is mechanically constrained inside the tip, there is hence no risk of parts which had become loose after the drop will fall out of the tip and into the mount of a patient during a subsequent scanning.

It is particularly advantageous to keep optical elements free from condensation when recording color along with 3D topographic characteristics. The color balance in recorded images can be distorted by levels of condensation still too slight to significantly deteriorate the signal needed to compute 3D topographic characteristics. Even slight distortions in color balance are highly noticeable for the human eye.

Disclosed is a 3D scanner for recording topographic characteristics of a surface of at least part of a body orifice, where the 3D scanner comprises:
    a main body;
    a mounting portion attached to the main body;
    a tip configured for being brought into close proximity of said body orifice surface when recording said topographic characteristics, where said tip can be sterilized in a steam autoclave and be mounted onto and un-mounted from the mounting portion of the 3D scanner; and an electrically powered element configured for providing an energy transfer to said tip, such that at least part of said tip is heated by said energy transfer, where the heating by energy transfer can raise the temperature of said optical element from 25 to 35 degrees C. within at most 10 minutes in 25 degrees C. ambient temperature while the scanner is supplied with a rated power input.

Disclosed is a 3D scanner for recording topographic characteristics of a surface of at least part of a body orifice, where the 3D scanner comprises:

a main body;

a mounting portion attached to the main body;

a tip configured for being brought into close proximity of said body orifice surface when recording said topographic characteristics, where said tip can be sterilized in a steam autoclave and be mounted onto and un-mounted from the mounting portion of the 3D scanner; and where said tip comprises at least one optical element that is at least partly exposed to the environment in the body orifice during scanning and where the optical element is glued to a sheet that is welded onto the body of the tip.

Disclosed is a scanner for recording the topographic characteristics of the surface of at least part of a body orifice, with a tip that during said recording may come into physical contact with at least part of said body orifice, where said tip:

can be mounted and unmounted from the remainder of the scanner without the use of any tool when unmounted, can be sterilized in a steam autoclave has at least one optical element that is at least partly exposed to the environment in the body orifice and where the optical element is glued to a sheet that is welded onto the body of the tip.

Disclosed is a 3D scanner for recording the topographic characteristics of the surface of at least part of a body orifice, with a tip that during said recording may come into physical contact with at least part of said body orifice, where said tip:

can be mounted and un-mounted from the remainder of the scanner without the use of any tool when un-mounted, can be sterilized in a steam autoclave has at least one optical element that is at least partly exposed to the environment in the body orifice and where said tip is heated by energy transfer from an electrically powered element other than a gas pump, and where said heating by energy transfer can raise the temperature of said optical element from 20 to 32 degrees C. within at most 60 minutes in 20 degrees C. ambient temperature while the scanner is supplied with its rated power input.

Disclosed is a 3D scanner for recording topographic characteristics of a surface of at least part of a body orifice, where the 3D scanner comprises:

a main body;

a mounting portion attached to the main body;

a tip configured for being brought into close proximity of said body orifice surface when recording said topographic characteristics, where said tip can be sterilized in a steam autoclave and be mounted onto and un-mounted from the mounting portion of the 3D scanner; and an electrically powered element configured for providing an energy transfer to said tip, such that at least part of said tip is heated by said energy transfer, where the heating by energy transfer can raise the temperature of said optical element from 25 to 35 degrees C. within at most 10 minutes in 25 degrees C. ambient temperature while the scanner is supplied with a rated power input.

Obtaining a three dimensional representation of the surface of an object by scanning the object in a 3D scanner can be denoted 3D modeling, which is the process of developing a mathematical representation of the three-dimensional surface of the object via specialized software. The product is called a 3D model. A 3D model represents the 3D object using a collection of points in 3D space, connected by various geometric entities such as triangles, lines, curved surfaces, etc. The purpose of a 3D scanner is usually to create a point cloud of geometric samples on the surface of the object.

3D scanners collect distance information about surfaces within its field of view. The "picture" produced by a 3D scanner describes the distance to a surface at each point in the picture.

For most situations, a single a scan or sub-scan will not produce a complete model of the object. Multiple sub-scans, such as 5, 10, 12, 15, 20, 30, 40, 50, 60, 70, 80, 90 or in some cases even hundreds, from many different directions may be required to obtain information about all sides of the object. These sub-scans are brought in a common reference system, a process that may be called alignment or registration, and then merged to create a complete model.

Iterative Closest Point (ICP) is an algorithm employed to minimize the difference between two clouds of points. ICP can be used to reconstruct 2D or 3D surfaces from different scans or sub-scans. The algorithm is conceptually simple and is commonly used in real-time. It iteratively revises the transformation, i.e. translation and rotation, needed to minimize the distance between the points of two raw scans or sub-scans. The inputs are: points from two raw scans or sub-scans, initial estimation of the transformation, criteria for stopping the iteration. The output is: refined transformation. The algorithm steps can be:

1. Associate points by the nearest neighbor criteria.
2. Estimate transformation parameters using a mean square cost function.
3. Transform the points using the estimated parameters.
4. Iterate, i.e. re-associate the points and so on.

An intra-oral or in-ear scanner may be configured for utilizing focus scanning, where the digital 3D representation of the scanned teeth is reconstructed from in-focus images acquired at different focus depths. The focus scanning technique can be performed by generating a probe light and transmitting this probe light towards the set of teeth such that at least a part of the set of teeth is illuminated. Light returning from the set of teeth is transmitted towards a camera and imaged onto an image sensor in the camera by means of an optical system, where the image sensor/camera comprises an array of sensor elements. The position of the focus plane on/relative to the set of teeth is varied by means of focusing optics while images are obtained from/by means of said array of sensor elements. Based on the images, the in-focus position(s) of each of a plurality of the sensor elements or each of a plurality of groups of the sensor elements may be determined for a sequence of focus plane positions.

The in-focus position can e.g. be calculated by determining the light oscillation amplitude for each of a plurality of the sensor elements or each of a plurality of groups of the sensor elements for a range of focus planes. From the in-focus positions, the digital 3D representation of the set of teeth can be derived.

3D modeling is the process of developing a mathematical, wireframe representation of any three-dimensional object, called a 3D model, via specialized software. Models may be created automatically, e.g. 3D models may be created using multiple approaches: use of NURBS curves to generate accurate and smooth surface patches, polygonal mesh modeling which is a manipulation of faceted geometry, or polygonal mesh subdivision which is advanced tessellation of polygons, resulting in smooth surfaces similar to NURBS models.

The present invention relates to different aspects including the device described above and in the following, and corresponding devices, each yielding one or more of the benefits and advantages described in connection with the first mentioned aspect, and each having one or more embodiments corresponding to the embodiments described in connection with the first mentioned aspect and/or disclosed in the appended claims.

The use of the invention is not limited to 3D scanners but can also be applied to 2D cameras, such as intraoral 2D cameras for acquiring a 2D image of a patient's teeth. This can e.g. be used in relation to caries detection where light from the 2D camera excite fluorescent materials in teeth and the 2D camera detect emitted fluorescence.

Disclosed is hence a 2D camera for recording topographic characteristics of a surface of at least part of a body orifice, where the 2D camera comprises:

a main body comprising a mounting portion;

a tip which can be mounted onto and un-mounted from said mounting portion, where said tip is configured for being brought into proximity of said body orifice surface when recording said topographic characteristics such that at least one optical element of the tip is at least partly exposed to the environment in the body orifice during said recording; and a heater system for heating said optical element, said heater system comprising a source of electromagnetic energy and a receptive element configured for receiving the electromagnetic energy and converting it into heat, where the generated heat is provided by way of thermal conduction directly to said optical element or indirectly through a heat conducting element;

where the tip can be sterilized in a steam autoclave when un-mounted from the main body of the 2D camera such that it subsequently can be reused.

Disclosed is a tip for a 2D camera for recording images of a surface of at least part of a body orifice, where the tip comprises:

a framework comprising a first opening configured for engaging a mounting portion of a main body of a 2D camera, and a second opening configured for allowing light received from a surface to enter the tip;

an optical element which at least partly is exposed to the environment in the body orifice during said recording; and means for providing heat to the optical element; where the tip can be sterilized in a steam autoclave when un-mounted from the mounting portion of the 2D camera such that it subsequently can be reused.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following, a few embodiments of the invention are described in detail. While the description also includes alternatives to some aspects of the embodiments, the described embodiments are only examples of many possible embodiments within the scope of this invention, and hence the invention is not limited to the following description.

In the following description, reference is made to the accompanying figures, which show by way of illustration how the invention may be practiced.

In the following, the reference numbers formatted as 1XX refers to features of the tip, and reference numbers formatted as 2XX refers to features of the main body of the scanner.

Figure 1:
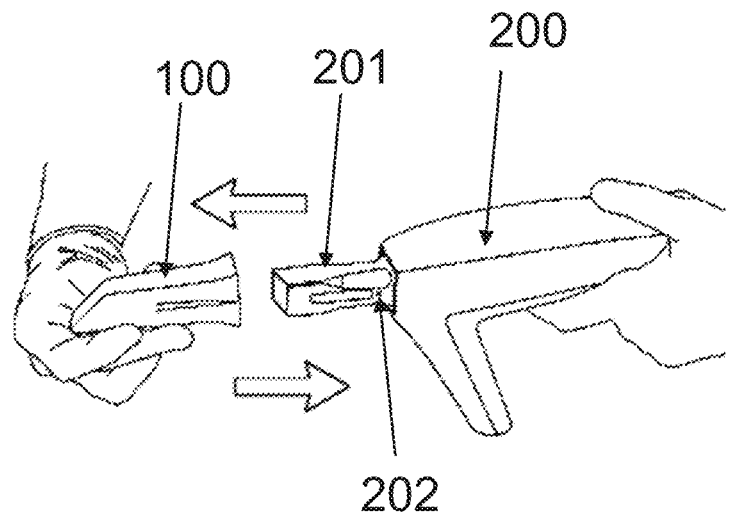
FIGS. 1 and 2 show how a tip can be arranged at the tube of a handheld scanner.

In FIG. 1, the scanner is an intraoral scanner that records the 3D topography of the teeth and parts of the surrounding issue. The user (typically the dentist) mounts the tip 100 on the mounting portion 201 which here is a tube that is a fixed part of the main body 200 of the handheld scanner. In the sense of the above general description, the tube is part of the main body of the scanner. The tube can have any form of cross section. A part of the optical path is inside the tube 201, substantially along the tube's axis.

At the end of a treatment, the user (dentist) unmounts the tip 100, which is then sterilized by at least autoclaving. Subsequently, the tip can be reused for treatment of another patient, essentially without any risk of cross contamination. The mounting and un-mounting operations are easy to perform for the user and require no tools. The tip 100 can simply be slid onto the tube 201, where it snaps onto balls 202, one pressed into each of two opposing sides of the tube (FIG. 1 shows only one side of the tube and thus only one ball). Other means for temporarily fixating the tip to the mounting portion of the 3D scanner can evidently be used instead of the balls.

Autoclavable in the sense of this invention means that the tip can be treated in a steam autoclave in the same manner as other dental instruments, e.g., a dental mirror, and subsequently used for scanning at least once.

Other parts of the main body of the 3D scanner are additional optical elements, an image sensor, processing electronics, a control unit configured for controlling the heating system and/or the topography recording, an outer shell, amongst others. All these other parts are not central to this invention and thus not shown specifically in FIG. 1. The 3D scanner can also comprise a light source. A light source is a central part in some embodiments of this invention.

Figure 2:
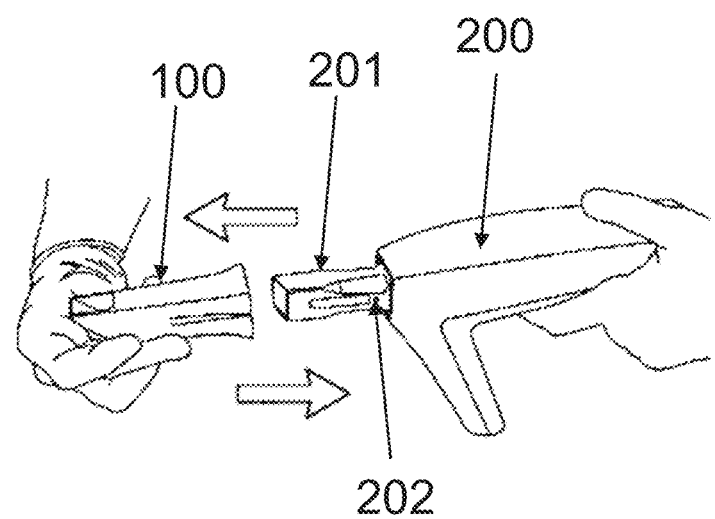

In the design illustrated in FIGS. 1 and 2, but not necessarily in general, the tip can be mounted in two positions on the tube 201. In FIG. 2, the tip 100 is in the opposite position relative to the tube 201 compared to the position illustrated in FIG. 1. Given that the tip also contains a mirror for directing the light path to and from the teeth, the scanner can thus be used for recording the upper or lower teeth, respectively, in a convenient manner. In this embodiment, the optical element in the tip is thus the mirror.

Figure 3:
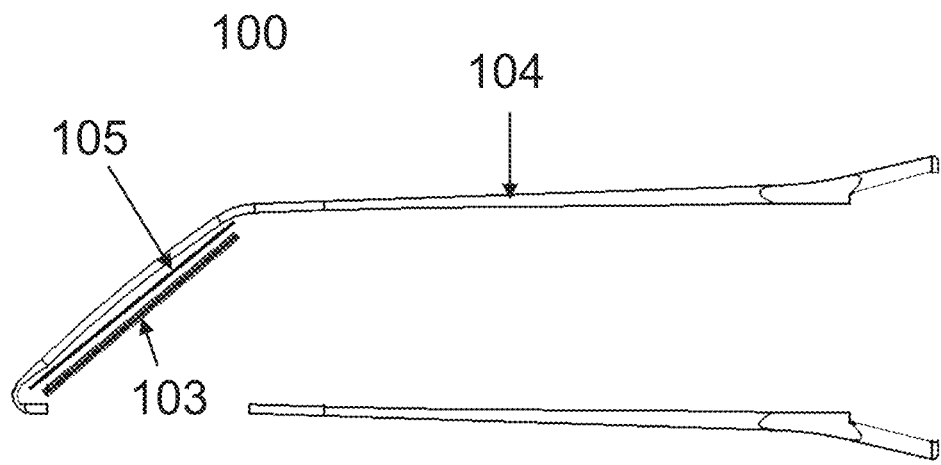
FIG. 3 shows a cross section of a tip.

FIG. 3 shows a cross section of the tip 100 containing the optical element, here a mirror 103, which is exposed to the environment in the body orifice during said recording. The framework 104 of the tip can be made of plastic by injection molding. Several plastic materials exist suitable for parts to be autoclaved, for example PSU. With appropriate glue, the mirror can be glued to the plastic. Because of the small number of glues that both can be autoclaved and adhere to autoclavable plastic, another method of fixing the mirror is to weld a thin sheet 105 made of some other material, e.g., metal to the plastic material and use glue to bond the mirror to that sheet. There is a much wider choice of autoclavable glues that bond metal to glass. The bonding requirements are high because commonly, a risk analysis will show that the tip must pass a drop test. A welding solution is described in detail below.

Figure 4:
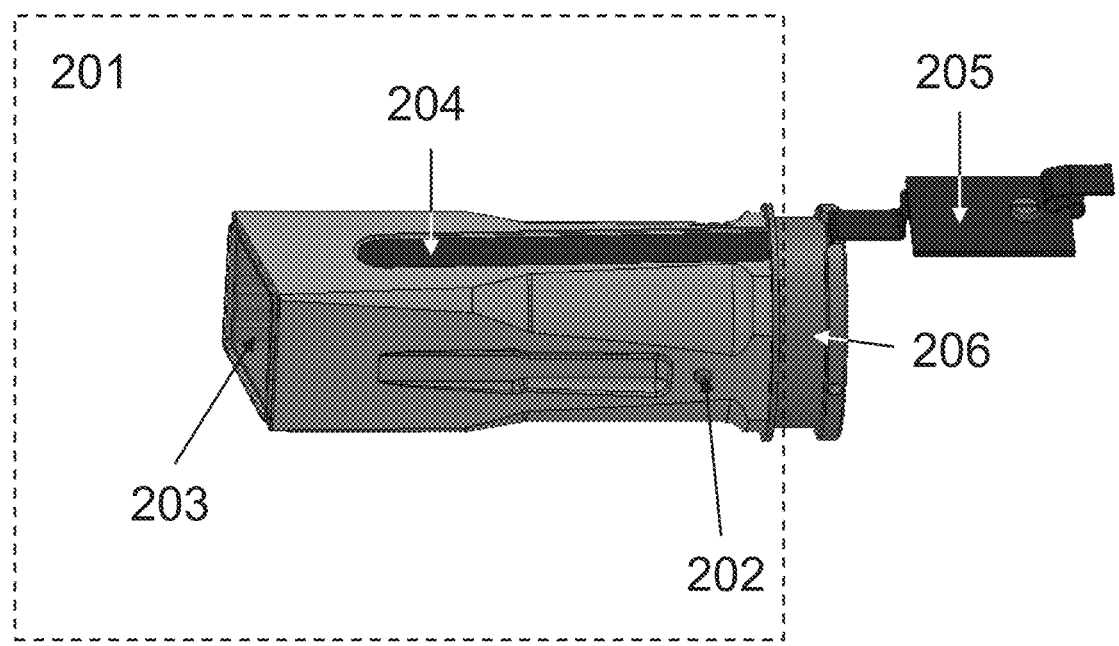
FIG. 4 shows a schematic drawing of a tube and some electronics.

FIG. 4 shows an example of an embodiment in which the tube 201 has a transparent front window 203. Because the tip is not closed (notice the opening at the mirror 103 in FIG. 3), the outward-facing surface of this window 203 is also exposed to the environment in the body orifice e.g. to the patient's breath, and without preventive measures, there would also be a risk of condensation occurring on this surface Condensation on the front window 203 in the tube 201 is prevented by heating the tube and thus the window 203 and the mirror 103 via thermal conduction. An electrical heater element 204 is placed on a side of the tube. The electrical heater element is electrically isolated from the tube 201, as to prevent any risk of electric shock to the patient and/or the operator. The heater element is resistive, and electric power to it is supplied by the source of electromagnetic energy which here is part of the scanner's electronics (partly shown as 205), which also are electrically isolated from the tube. The scanner is supplied with electrical power from mains and/or a battery. Note that the heater electrical element 204 in practice is covered by a thin sheet of electrically insulating material; as it would hide the heater element is it however not shown in FIG. 4.

FIG. 4 also shows a plastic ring 206 that provides electrical insulation between the tube 201 and the main body of the 3D scanner, for electrical safety reasons. The plastic material also limits the conduction of waste heat from the main body of the 3D scanner to the tip, indicating the importance of the invention since heating of the tip would be very inefficient if the heater was arranged in the main body of the 3D scanner. One ball 202 onto which the tip can snap is also illustrated in the figure.

Figure 5A:
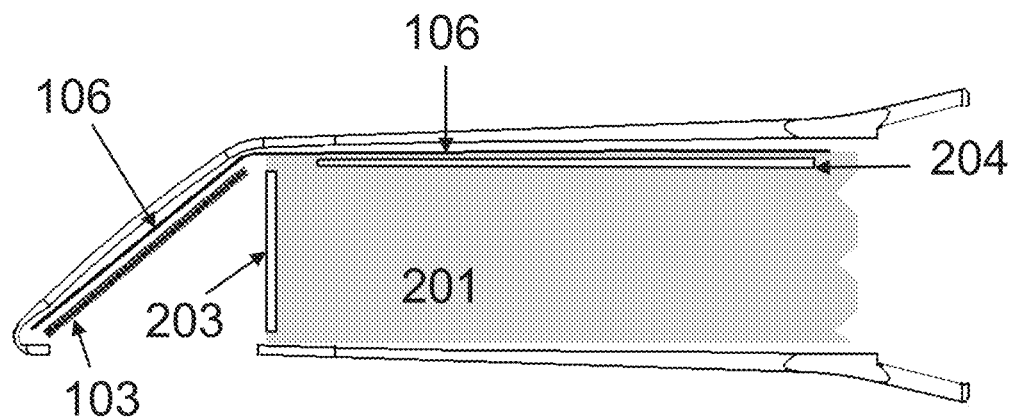
FIGS. 5a and 5b show an example of a scanner tip according to the present invention.

In FIG. 5a, the heat conducting element comprises a sheet 106 arranged in the scanner tip. The sheet 106 is at least partly made of a heat conducting material and runs along the inside of the tip, extending from behind the mirror 103 to the region that is designed to come into physical contact with the tube (therefore the two arrows in the figure pointing at these two major sections of the sheet 106). When the tip is mounted on the tube and the tube is heated by providing electromagnetic energy to the electrical heater element 204, the generated heat is transferred by thermal conduction to the tip and all the way to the mirror 103 via the heat conducting sheet 106. Note that the sheet 106 can also be welded to the tip material in the same manner as the smaller sheet 105. When the tube is heated the temperature of the mirror 103 and of the window 203 increases and condensation of moisture on the window is prevented.

Even though the sheet 106 is designed to come into physical contact with the tube 201, manufacturing tolerances may result in a situation where this contact is poor, or where there even is a small gap between the sheet and the tube. To provide a design that fulfills the purpose and is robust to manufacturing tolerances, providing the electromagnetic energy to the receptive element and/or converting the electromagnetic energy to heat can also be through induction. This is implemented by the electrical heater element 204 having its wiring arranged as a coil and supplied with a time variant current, such that the electrical heater element also can function as an element configured for transferring the electromagnetic energy. The wiring in the electrical heater element may be implemented as tracks on a printed circuit board (PCB). In the design shown in this figure, the sheet 106 then functions both as the receptive element converting the electromagnetic energy into heat and as the heat conducting element though which the heat is provided to the optical element. The receptive element hence coincides with the heat conducting element. Note that the coil is seen from the side in FIG. 5a, and because of its small height, it cannot be properly visualized in the figure.

In some embodiments, the sheet 106 is made of magnetic stainless steel. A two-layer solution with a wear-resistant, induction-perceptive metal facing the tube 201 and graphite on the side facing the framework 104 of the tip could be a suitable alternative.

The sheet 106 must not come off when mounted on/off the tube even multiple times. Likewise, the mounting operation must not create forces by which the mirror in the tip can become detached. One solution for these problems is to partly mold the sheet into the tip. Because the tip is entered into the patient's mouth, its height should be small. Therefore, the sheet is preferably thin, such as with a thickness of less than 2 mm, such as with a thickness of less than 1 mm, such as with a thickness of less than 0.5 mm, such as with a thickness of less than 0.3 mm.

Figure 5B:
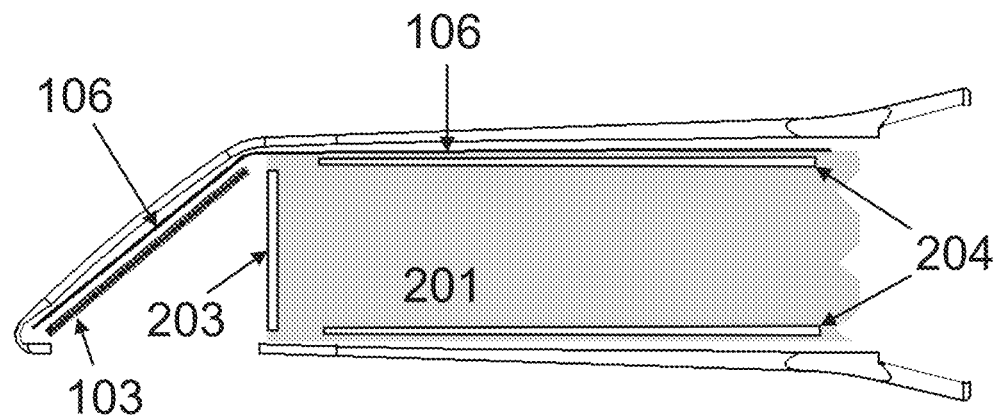

A possibility of mounting the tip in two positions (facing up/down as shown in FIGS. 1 and 2) requires that heating be possible in both positions. To obtain an effective transfer of energy by induction under both positions, multiple electrical heater elements 204 with coils can be provided, for example at opposing sides of the tip (FIG. 5b), with either one designed to be in contact with a straight sheet, a strip, that runs along one side of the inside of the tip. The tip itself can remain unchanged relative to FIG. 5a.

Figure 6A:
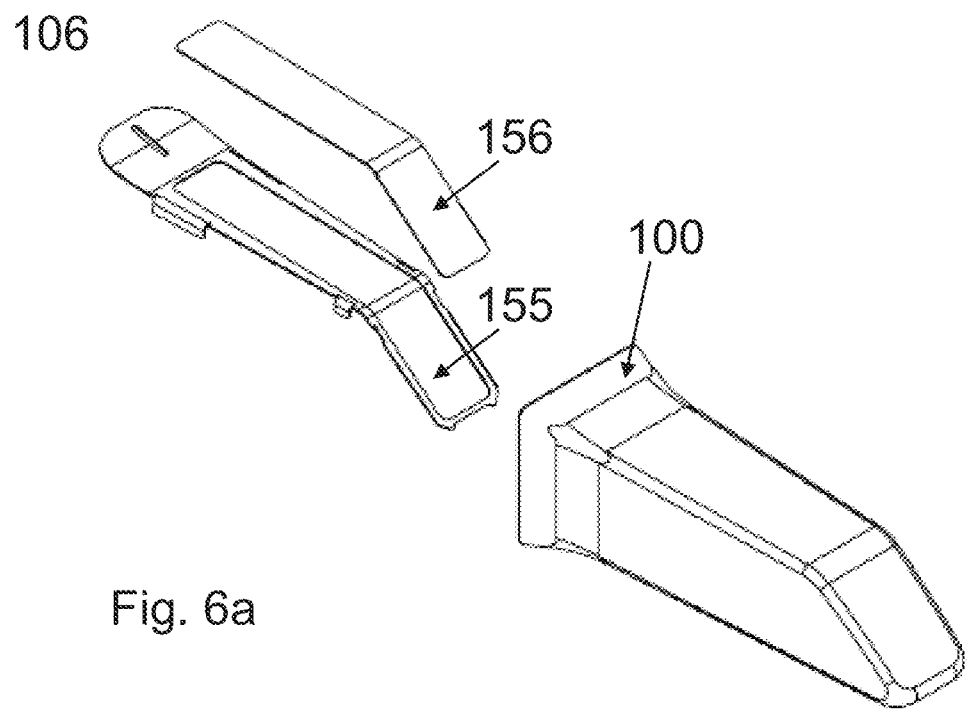
FIGS. 6a and 6b show a tip comprising a multi-layer heat conducting element.

Another possibility similar to the one of FIG. 5a is shown in FIG. 6a. Here, the sheet 106 making up part of the heat conductive element is comprised of two layers, a heat conducting layer 156 made of eGraf and a protective layer 155 made of stainless steel. A recess has defined in the protective layer by controlled etching and the heat conducting layer is arranged in said recess. The arrangement of the heat conductive layer and the protective layer is such that the protective layer shields the heat conducting layer from abrasion on the mounting portion of the main body when the tip is mounted on the 3D scanner. This stainless steel need not be magnetic.

The stainless steel protective layer protects the eGraf layer when both are mounted inside the tip 100. This is advantageous because eGraf alone would get damaged in a medical instrument washer. On the other hand, stainless steel alone would only provide inferior thermal conductance, with a thermal conductivity about 25 times small than eGraf's.

Another advantage of eGraf is its anisotropy in thermal conductivity, which can be exploited to achieve a high heat transfer towards the optical element, while keeping undesired heat transfer towards the tip and thus its outer surface, which may have patient contact, small. In one realized configuration, the thickness of the heat conducting layer is 0.4 mm.

Figure 6B:
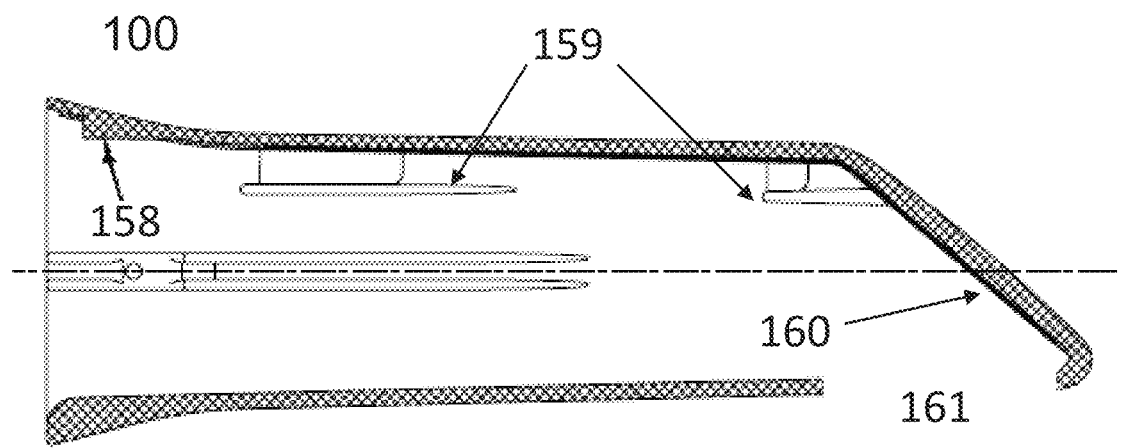

Details of the mounting of the eGraf-steel heat conductive element are shown in FIG. 6b, which shows that the insertion of the conductive element can be guided mechanically by "rails" 159 inside the tip (100). In the example, attachment of the sheet to the tip is by heat stacking, on area 158. A mirror (not shown) can be glued to the face 160 of the stainless steel layer. Neither the multi-layer sheet making up the heat conductive element nor the compound of sheet and mirror can fall out through the opening 161 of the tip, both due to the constraint provided by the "rails" 159, and due to a conical shape of the sheet, with the end holding the mirror being the narrower one (c.f., FIG. 6a) and the broader part of the sheet being large than the opening 161. The tip shown in FIGS. 6a and 6b can be mounted on a tube with one or multiple heater elements (c.f., FIGS. 5a and 5b).

Figure 7:
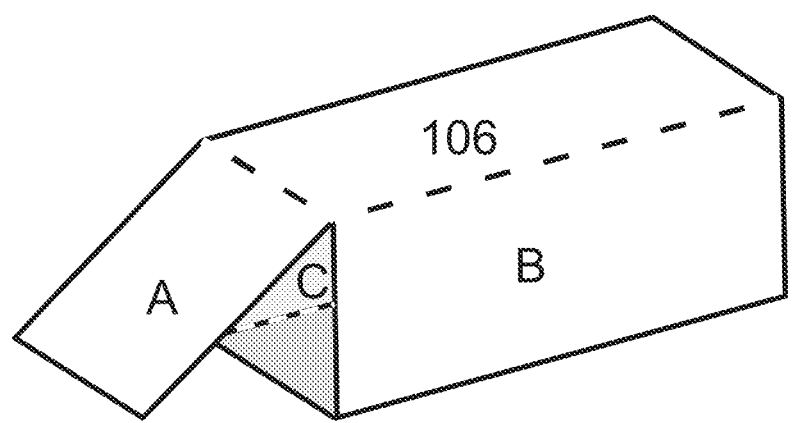
FIG. 7 shows a 3D drawing of an example of a sheet.

Another solution that achieves effective inductive heating in both positions is to leave the tube unchanged relative to FIG. 5a, but to provide a more complex sheet that is folded to cover multiple sides of the inside of the tip, with different sections designed to come into contact with only one heater element. FIG. 7 is a 3D drawing of an example of such a sheet 106. The more complex sheet could be created by folding, bending, and/or welding the edges. The mirror (not shown in FIG. 7) would be attached to the back side (not visible here) of the flap A in FIG. 7. To improve heat conduction, the flap A can be connected to face B, but this is not shown because it would render FIG. 7 difficult to understand. Likewise, face C can be connected to flap A.

Figure 8:
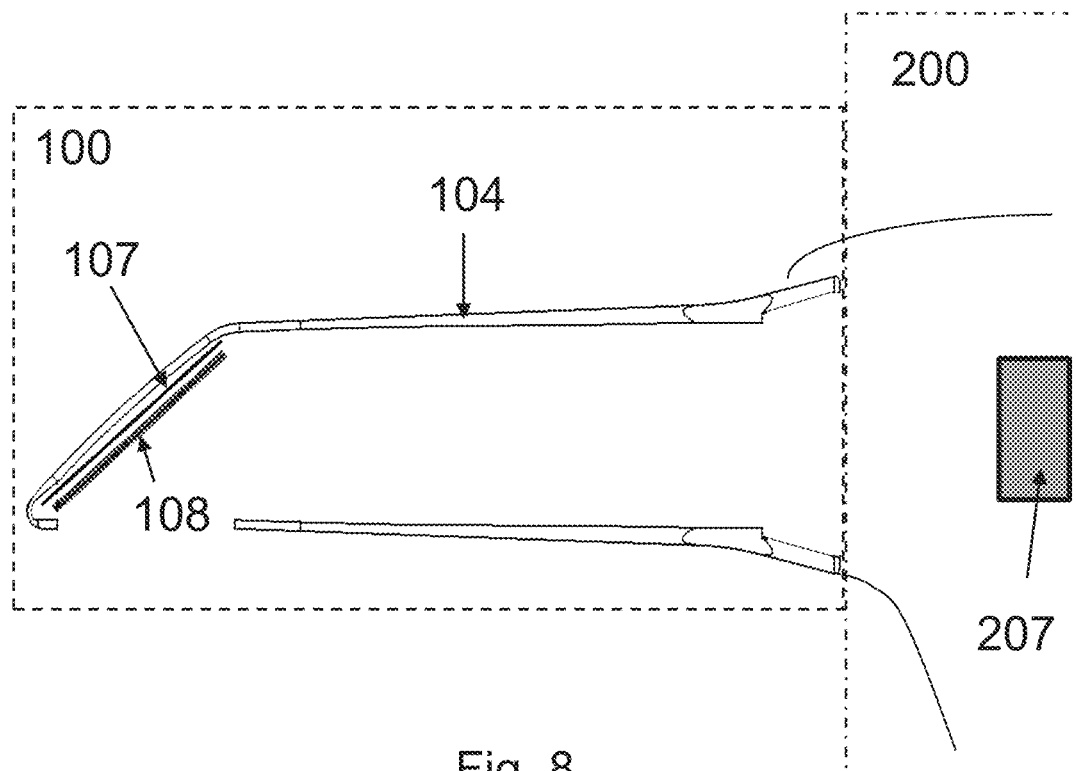
FIG. 8 shows an example of an embodiment in which energy transfer is by electromagnetic radiation.

FIG. 8 shows an example of an embodiment in which energy transfer is by electromagnetic radiation. Here, the light source 207 in the scanner is a dual-color LED, and the mirror 108 is a dichroic mirror. In such an embodiment, the light source is the source of electromagnetic energy and is located in the main body of the scanner. The mirror reflects one of the two wavelengths of light generated by the LED, but lets the other pass. The portion of light that is transmitted through the dichroic mirror is then absorbed by a receptive element 107, which can be the same as the sheet 105 illustrated in FIG. 3. As the receptive element 107 absorbs the light, it heats up, and hence it directly heats the dichroic mirror 108 that it is in physical contact with. For practical purposes, there is a thin layer of glue in between 107 and 108, bonding these two elements to each other. The wavelength of the transmitted portion may be longer or shorter than the wavelength of the portion directed towards the teeth by the dichroic mirror. In some embodiments, at least one wavelength is not visible, such as UV or IR light.

Figure 9:
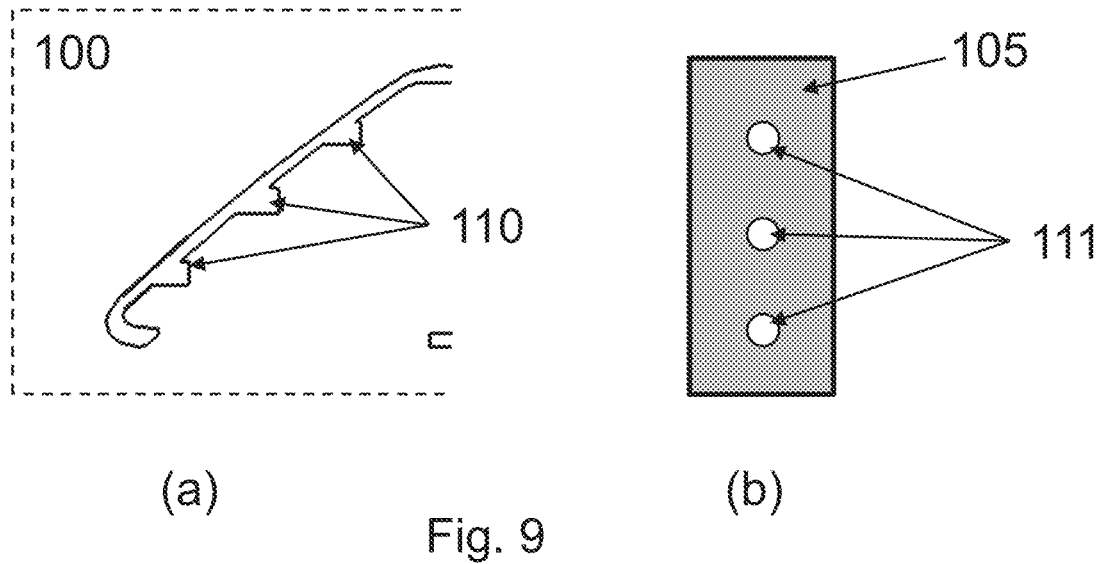
FIG. 9 shows a welding solution for the tip.

FIG. 9 shows a welding solution for the tip 100. Part (a) of the figure shows a cross section of the front part of the tip, from the same perspective as FIG. 3. The design is for injection molding and has three studs 110. Part (b) of the figure shows a matching thin metal sheet 105 shown for clarity from the top, from a perspective orthogonal to that of part (a). The sheet has three holes 111. The sheet is assembled such that the studs 110 penetrate through the holes 111. Then, a hot tool is pressed onto the tips of the studs such that they melt, flatten, and thus hold the metal sheet in place. Finally, a mirror 103, 108 can be glued to the metal sheet (not shown in FIG. 9). The sheet 105 could also be made of a non-metallic material. Several autoclavable glues are available that can bond an autoclavable metal to glass or to other metal, i.e., the substrates of which mirrors are typically made. For such materials autoclavable metal can be advantageous.

Figure 10:
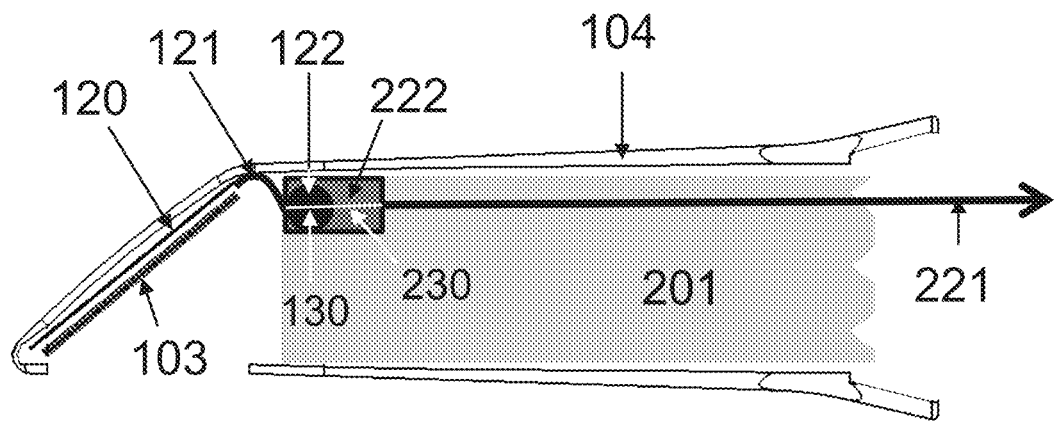
FIG. 10 shows an embodiment with an electrically powered, resistive heater element.

FIG. 10 shows an embodiment of the tip with a receptive element 120 located behind the mirror 103 and touching that mirror. The receptive element 120 comprises a resistive material and is electrically powered i.e. the electromagnetic energy is converted by passing an electrical current through the resistive material. Elements configured for transferring the electromagnetic energy to the receptive element are arranged in the tube and in the tip. In the tip these elements include a two-conductor cable 121 with a contact surface 122. In the tube 201 these elements contain another contact surface 222, connected with a two-conductor cable 221 to the source of electromagnetic energy (a power source not shown in FIG. 10) located in the main body of the scanner or elsewhere. When the tip is slid onto the tube, physical and electrical contact is established between the two contact surfaces 122 and 222, allowing electromagnetic energy to be transmitted to the receptive element 120 which thus can convert the electromagnetic energy to heat which is directly provided to the mirror 103 by thermal conduction. Note that to provide the electrical circuit, the contact surface 122 is separated into two zones by some electrical insulation 130, and in a matching configuration, the contact surface 222 is separated into two zones by some electrical insulation 230, with each conductor in the cable 121 and 221, respectively, connected to one zone. Alternatively 122 and 222 are divided in two areas and mounted on two opposite sides of the tip.

Figure 11:
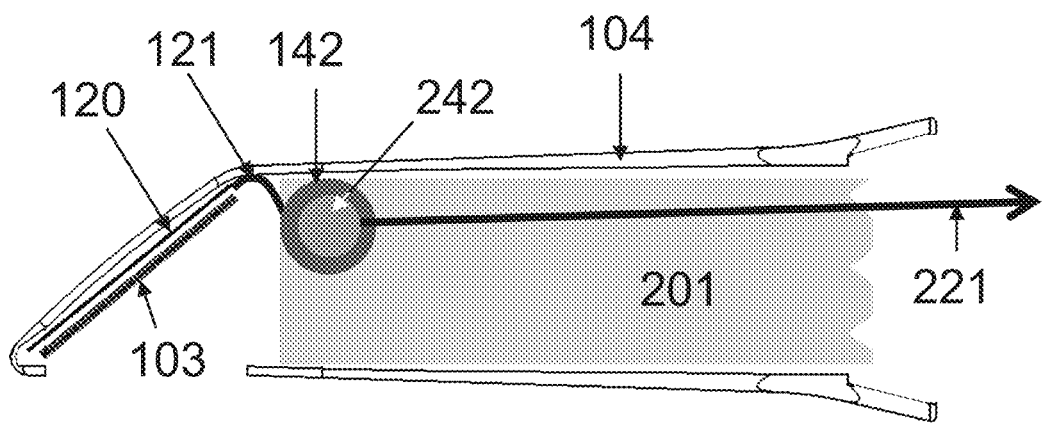
FIG. 11 shows an embodiment using wireless transmission of electrical energy.

FIG. 11 shows an embodiment which is a modification of the one in FIG. 10, now with the elements configured for transferring the electromagnetic energy to the receptive element being based on wireless transmission of electromagnetic energy. The elements 142 and 242 include coils, with power-transmitting element 242 being connected to the source of electromagnetic energy (a power source not shown in FIG. 11) located in the main body of the scanner or elsewhere. Electromagnetic energy can thus be transmitted in a wireless manner to the power-receiving element 142 which is electrically connected to a receptive element, which here is a resistive electrical heater element 120, by a two-conductor cable 121, such that the mirror 103 can be heated by way of thermal conduction. For wireless power transfer to be efficient, the coils on elements 142 and 242 should be designed to be aligned when the tip is mounted on the tube. All other elements in FIG. 11 are to be understood as in FIG. 10. Wireless transfer of electromagnetic energy can be advantageous because corrosion of the contact surfaces 122 and 222 after repeated autoclaving may lead to poor electrical contact in the embodiment of FIG. 10.

Figure 12:
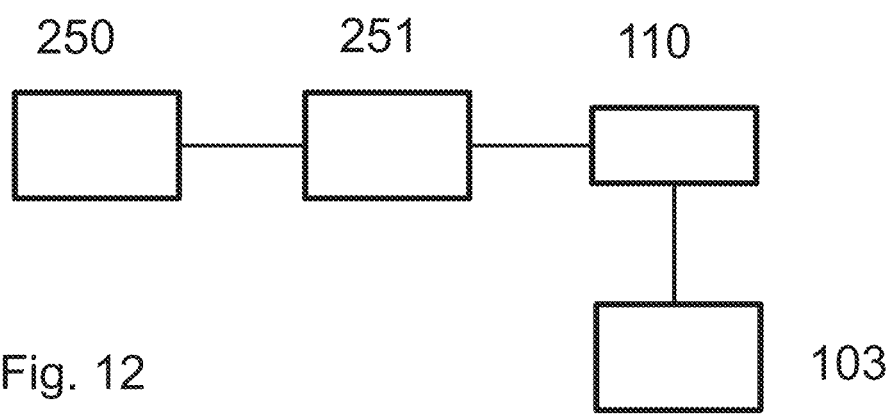
FIG. 12 shows schematic representation of the 3D scanner.

FIG. 12 shows schematic representation of the 3D scanner. The source of electromagnetic energy 250 is arranged in the main body of the scanner or in another element which the main body is connected to, for example an external power source. From there it provides electromagnetic energy to the receptive element 110 through one or more elements 251 configured for transferring the electromagnetic energy. The receptive element 110 is configured for receiving the electromagnetic energy and converting it into heat. The generated heat is provided by way of thermal conduction directly to the optical element 103 in the tip of the 3D scanner or indirectly through a heat conducting element.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

REFERENCES

[1] Infektionsprävention in der Zahnheilkunde—Anforderungen an die Hygiene. Mitteilung der Kommission für Krankenhaushygiene and Infektionsprävention beim Robert Koch-Institut. Bundesgesundheitsblatt—Gesundheitsforschung—Gesundheitsschutz 2006:4
[2] Centers for Disease Control and Prevention. Guidelines for Infection Control in Dental Health-Care Settings—2003. MMWR 2003; 52 (No. RR-17).

The invention claimed is:

1. A 3D scanner for recording topographic characteristics of a surface of at least part of a body orifice of a patient, where the 3D scanner comprises:
a main body comprising a mounting portion;
a tip configured to be mounted onto and un-mounted from said mounting portion, where said tip is configured for being brought into proximity of said body orifice surface when recording said topographic characteristics such that at least one optical element of the tip is at least partly exposed to the environment in the body orifice during said recording;
a heater system for heating said optical element, said heater system comprising a source of electromagnetic energy and a receptive element configured for receiving the electromagnetic energy and converting the electromagnetic energy into heat; and
a control system configured to control heating of the optical element;
where the tip is configured to be sterilized when un-mounted from the main body of the 3D scanner such that the tip subsequently can be reused,
where said heater system comprises one or more elements configured for transferring the electromagnetic energy from the source to the receptive element,
where the optical element comprises a mirror and the receptive element comprises a resistive element arranged behind the mirror, and where the elements configured for transferring the electromagnetic energy are configured for transferring the electromagnetic energy from the main body to the receptive element.

2. The scanner according to claim 1, where said mounting portion comprises a tube, the tube configured for the tip to be mounted onto.

3. The scanner according to claim 1, where said heater system and said tip are configured to provide that the temperature of said optical element can be raised from 20 to 32 degrees C. within at most 60 minutes in 20 degrees C. ambient temperature while the scanner is supplied with a rated power input.

4. The scanner according to claim 1, where the scanner is configured to provide that the heater system provides the heat to the optical element during at least a part of the recording.

5. The scanner according to claim 1, where said body orifice is a human mouth and the tip is configured for being brought into the patient's mouth.

6. The scanner according to claim 1, where the source of electromagnetic energy comprises a power source.

7. The scanner according to claim 1, where the mounting portion and the tip are configured such that the tip can be mounted in multiple positions.

8. The scanner according to claim 1, where the tip is configured such that the tip can withstand being washed in a medical instrument washer, such that the tip subsequently can be reused.

9. The scanner according to claim 1, where the tip is configured to be sterilized in a steam autoclave when un-mounted from the main body of the 3D scanner such that the tip subsequently can be reused.

* * * * *